(12) United States Patent
Rafferty et al.

(10) Patent No.: US 8,784,737 B2
(45) Date of Patent: Jul. 22, 2014

(54) INTRODUCING AN ANALYTE INTO A CHEMICAL ANALYZER

(75) Inventors: David Rafferty, Webster, TX (US); Michael Spencer, Manvel, TX (US); James Wylde, Oak Leaf, TX (US); Pedro Ojeda, Pflugerville, TX (US); Thomas Bowden, League City, TX (US)

(73) Assignee: 1st Detect Corporation, Austin, TX (US)

( * ) Notice: Subject to any disclaimer, the term of this patent is extended or adjusted under 35 U.S.C. 154(b) by 0 days.

(21) Appl. No.: 13/367,755

(22) Filed: Feb. 7, 2012

(65) Prior Publication Data

US 2012/0223226 A1 Sep. 6, 2012

Related U.S. Application Data

(60) Provisional application No. 61/440,267, filed on Feb. 7, 2011.

(51) Int. Cl.
*G01N 30/02* (2006.01)
*G01N 30/08* (2006.01)
*G01N 1/40* (2006.01)
*G01N 7/04* (2006.01)
*G01N 1/22* (2006.01)
*G01N 30/60* (2006.01)

(52) U.S. Cl.
CPC *G01N 1/405* (2013.01); *G01N 7/04* (2013.01); *G01N 1/2214* (2013.01); *G01N 30/08* (2013.01); *G01N 30/6069* (2013.01); *G01N 2030/085* (2013.01)
USPC ........................................................ 422/88

(58) Field of Classification Search
CPC ......... G01N 7/04; G01N 27/12; G01N 30/00; G01N 30/08; G01N 1/405; G01N 30/6069; G01N 2030/085; G10N 1/2214

USPC ................ 422/88, 89, 527; 73/23.35, 23.41; 96/108, 112
See application file for complete search history.

(56) References Cited

U.S. PATENT DOCUMENTS

| | | |
|---|---|---|
| 5,667,713 A | 9/1997 | Kuma |
| 6,171,378 B1 | 1/2001 | Manginell et al. |
| 6,503,298 B1 | 1/2003 | Monzyk et al. |
| 7,727,314 B1 | 6/2010 | Manginell et al. |
| 7,799,280 B1 | 9/2010 | Manginell et al. |
| 2004/0231509 A1 | 11/2004 | Hartlein |
| 2007/0180933 A1 | 8/2007 | Grate et al. |
| 2008/0121103 A1 | 5/2008 | Boyle et al. |
| 2008/0148815 A1 | 6/2008 | Lucas et al. |
| 2009/0028208 A1 | 1/2009 | Martin |
| 2009/0090197 A1 | 4/2009 | Finlay et al. |
| 2010/0144049 A1 | 6/2010 | Combes et al. |

FOREIGN PATENT DOCUMENTS

| | | |
|---|---|---|
| WO | WO2005001426 A2 | 1/2005 |
| WO | WO2010014950 A1 | 2/2010 |

OTHER PUBLICATIONS

European Authorized Officer, Igor Cantalapiedra, International Search Report and Written Opinion, International Application No. PCT/US2012/024138 dated May 4, 2012.

*Primary Examiner* — Lyle Alexander
(74) *Attorney, Agent, or Firm* — Finnegan, Henderson, Farabow, Garrett & Dunner LLP

(57) ABSTRACT

A chemical pre-concentrator includes a conduit defining a flow path between two ends and having a heating element disposed within the conduit, such that the heating element has at least one sorbent material deposited directly on at least a portion of a conductive surface of the heating element. Some such heating elements are in the form of electrically conductive strips defining both a plurality of apertures through the strip and a series of undulations spaced along the flow path.

37 Claims, 5 Drawing Sheets

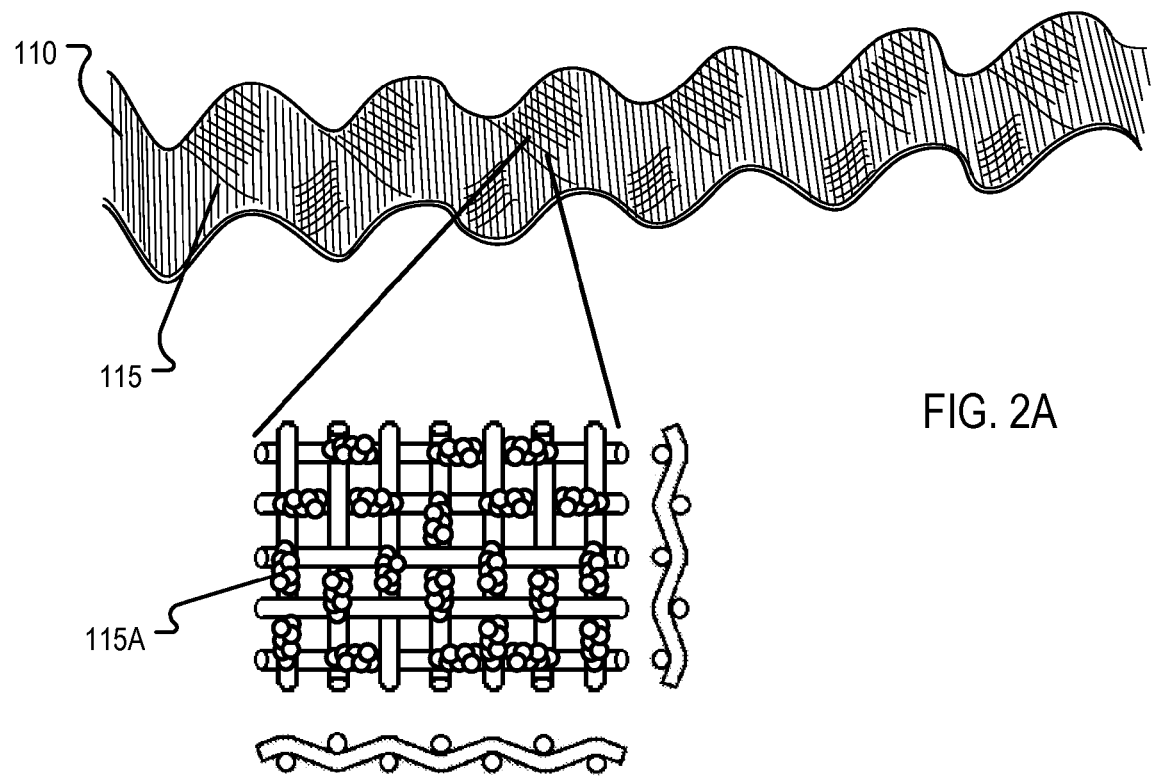
FIG. 2A
FIG. 2B
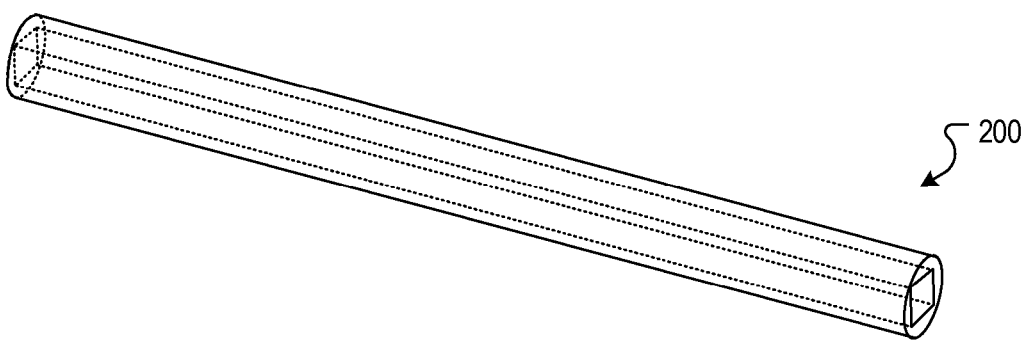
FIG. 2C

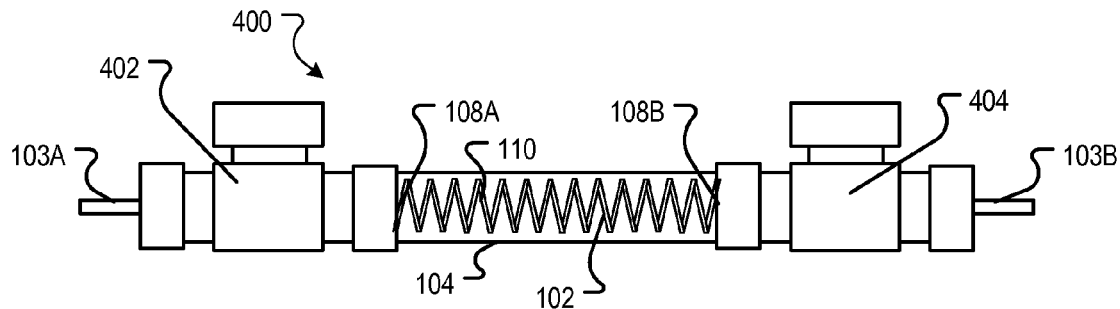
FIG. 4
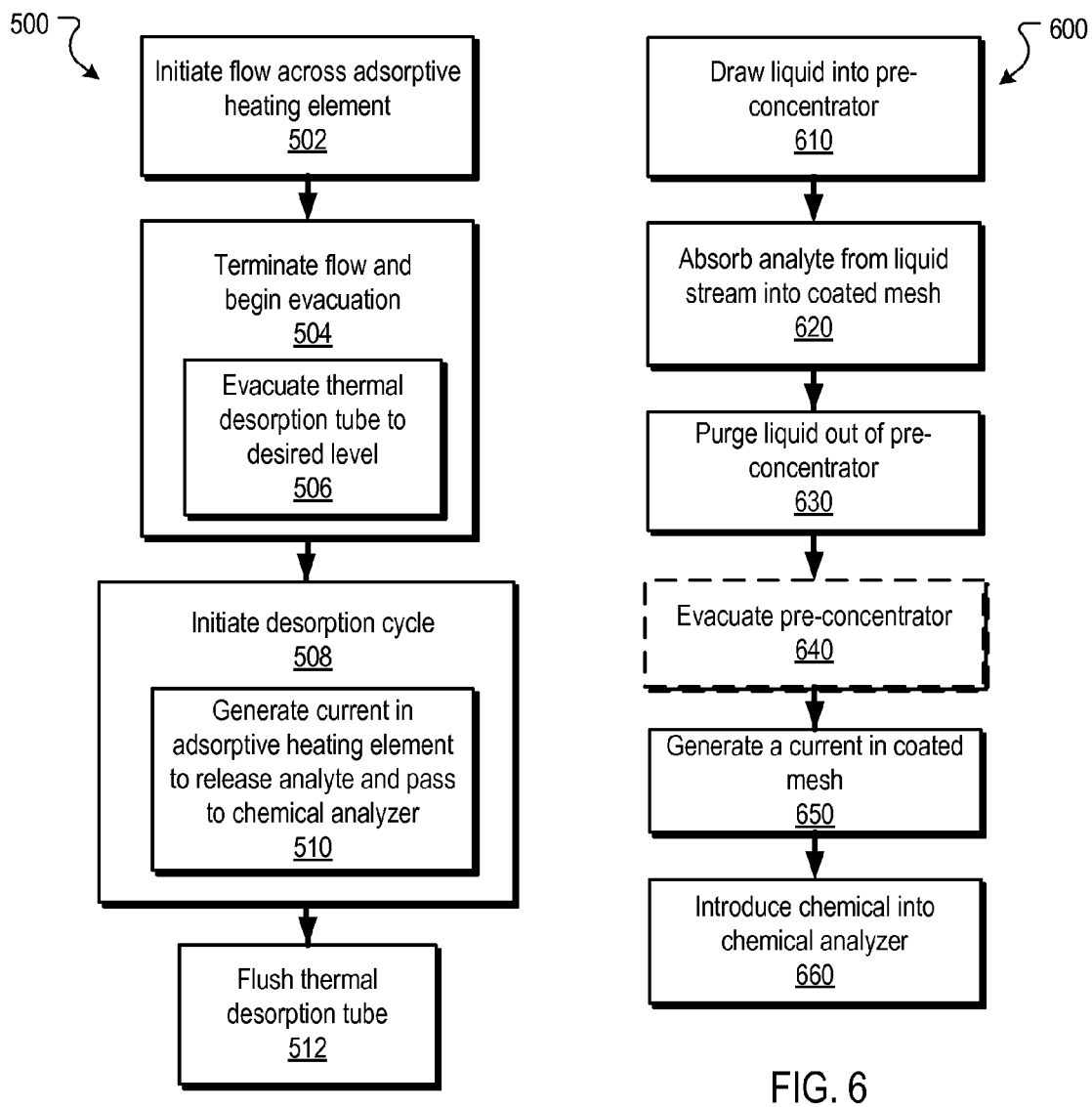
FIG. 5
FIG. 6

INTRODUCING AN ANALYTE INTO A CHEMICAL ANALYZER

CROSS-REFERENCE TO RELATED APPLICATIONS

This application claims the benefit of priority to U.S. Provisional Application Ser. No. 61/440,267, filed on Feb. 7, 2011, the entire contents of which are incorporated by reference herein.

BACKGROUND

This specification relates to introducing an analyte into a chemical analyzer for analysis.

Chemical analysis tools such as gas chromatographs ("GC"), mass spectrometers ("MS"), ion mobility spectrometers ("IMS"), and various others, are commonly used to identify trace amounts of chemicals, including, for example, chemical warfare agents, explosives, narcotics, toxic industrial chemicals, volatile organic compounds, semi-volatile organic compounds, hydrocarbons, airborne contaminants, herbicides, pesticides, and various other hazardous contaminant emissions. A summary of available detection technologies is contained in Yin Sun and Kowk Y Ong, Detection Technologies for Chemical Warfare Agents and Toxic Vapors, 2005, CRC Press, ISBN 1-56670-668-8 ("Sun & Ong").

Chemical detectors have a minimum concentration of analyte in a matrix that can be detected. For some chemicals, particularly threats, it is desirable to detect at extremely low concentrations compared to the sensitivity limit of typical instruments. For example, in some uses, instruments must be capable of detecting chemicals present to at or below 1 ppb to be effective. Table 1, below, is adapted from shows the Immediate Danger to Life and Health (IDLH) values for several common Chemical Warfare Agents (CWAs). As can be seen from examination of this table, these agents are dangerous at concentrations down to 2 ppb, hence instruments intended to detect various CWAs must be able to detect below the corresponding IDLH.

TABLE 1

IDLH values of common CWAs. Adapted from Sun & Ong

| CWA | CAS | IDLH (ppm) |
| --- | --- | --- |
| GA | 71-86-6 | 0.030 |
| GB | 107-44-8 | 0.030 |
| GD | 96-64-0 | 0.008 |
| GF | 329-99-7 | 0.030 |
| VX | 50782-69-9 | 0.002 |

Further, many explosives have very low volatility indexes and as such, emit a very low amount of vapor into the surrounding air. In the case of mass spectrometers, which typically require that the chemical sample be introduced into the instrument in a gaseous form, low sensitivity limits would be particularly useful. In particular, for mass spectrometers to effectively detect the presence of explosives simply by analyzing the air in the proximity of the instrument, extremely low sensitivity limits are desirable (ideally parts per trillion).

To facilitate this low concentration detection, some systems include a chemical pre-concentrator to increase the apparent concentration of samples being introduced to the chemical analyzer. For example, the apparent concentration of a sample introduced into an analyzer can be increased by using a membrane between the sample inlet and the chemical analyzer to remove or block certain species, while allowing target species to flow into the analyzer. While membrane inlets have been proven effective in commercial applications, they are typically limited to small concentration gains (<100) and are selective in the types of materials that are allowed through the membrane. An alternative approach is to use solid sorbent tubes to trap the species of interest. Conventional sorbent tubes are typically composed of a metal or glass tube packed with glass fibers or beads coated with or comprised of absorptive material, solid absorbent (e.g., calcium chloride, silica gel), or a variety of sorbent materials suited for the particular application. It should be noted that the terms absorption (implying an interaction of the analyte with the bulk material) and adsorption (implying an interaction with the surface of a material) are both used interchangeably. The specific mechanism of collecting the analyte is material dependent and all forms of collection are covered by the scope of this disclosure. The tubing is typically wrapped in Nichrome wire which heats the tubing when an electrical current is passed through it. During the collection phase, a sample is passed (e.g., by carrier gas, or liquid) through the tube while the sorbent material sorbs the analyte. These sorbents are then heated, releasing the analyte into the analyzer in a much shorter time than they were sorbed, thus increasing the concentration "seen" by the chemical analyzer.

Indirectly heating the sorbent material often results in various inefficiencies. For example, the sorbent material within the tube typically provides poor heat conduction paths, thus hindering the heat flow to the interior of the tube. Further, additional power and time is typically required to compensate for the loss of heat into the surroundings. In addition, the sorbent material often impedes the passage of the carrier gas during sampling and desorption. Still further, while large gains in concentration are possible, conventional sorbent tubes may have other drawbacks: 1) there can be a substantial amount of time and power required to sorb & desorb sufficient material, 2) the various locations on the sorbent material are not heated simultaneously thus releasing analyte at different times; hence reducing the apparent concentration seen at any one sample time and broadening the overall resolution of the pre-concentrator, 3) reactions between the analyte, sorbent, and background matrix can skew measurements by introducing unknowns into the chemical analyzer, 4) they can be very selective in that the gain measured between different sorbents can vary dramatically, 5) the sorbent material is not heated uniformly thus some analytes will be released at different times and to varying extents.

SUMMARY

In general, one innovative aspect of the subject matter described in this specification can be embodied in a chemical pre-concentrator including a conduit defining a flow path between two ends, and a heating element disposed within the conduit, the heating element having an electrically conductive surface and at least one sorbent material deposited directly on at least a portion of the surface. In some implementations, the conduit is an elongated conduit and the heating element is in the form of an electrically conductive strip defining both a plurality of apertures through the strip and a series of undulations spaced along the flow path.

These and other embodiments can each optionally include one or more of the following features. An internal cross-section of the conduit can be substantially rectangular transverse to the flow path. The heating element can be a mesh of electrically conductive filaments. The heating element can be partially coated with at least a plurality of sorbent materials and, in some examples, the plurality of sorbent materials can be disposed serially along the flow path. The heating element can include two electrodes configured to be coupled to a power source. The pre-concentrator may further include control circuitry configured to control an evacuation of the conduit to form a vacuum environment within the conduit. The control circuitry can be configured to conduct current through the heating element to desorb at least one analyte from the at least one sorbent material after evacuating the conduit. The control circuitry communicates with at least one flow control device disposed within or coupled to the pre-concentrator.

The conduit can define a flow restrictor at least at one of the two ends. The heating element can define a plurality of apertures through the heating element. The heating element can define a series of undulations spaced along the flow path. The series of undulations can form a plurality of sorbent surfaces along the flow path and are arranged such that flow along the flow path will be incident to the sorbent surfaces to enhance sorption of an analyte. The series of undulations can be of a size, with respect to a cross-sectional area of the flow path, sufficient to increase local turbulence of an air flow along the flow path. The heating element can define both a plurality of apertures through the heating element and a series of undulations spaced along the flow path, the plurality of apertures and undulations forming a plurality of screens along the flow path and arranged such that flow along the flow path will be incident to the screens to enhance sorption of an analyte. The flow path can extend along both sides of the heating element. The strip can be of generally constant thickness, such that the undulations are present on both sides of the strip.

According to another aspect, introducing an analyte into a chemical analyzer for analysis is accomplished by: providing a desorption tube comprising a conduit defining a flow path between two ends and having a heating element at least partially coated with at least one sorbent material disposed therein and such that the heating element is an electrical conductor; evacuating the conduit to form a vacuum environment within the conduit; then, conducting current through the heating element to desorb the analyte from the sorbent material; and transferring the desorbed analyte into the chemical analyzer. In some cases, the heating element can be in the form of an electrically conductive strip defining both a plurality of apertures through the strip and a series of undulations spaced along the flow path. Further, in some examples, providing a desorption tube may include utilizing the desorption tube to supply the desorbed analyte. A first of the two ends may be an inlet, and introducing the analyte into the chemical analyzer may further include introducing a test sample into the inlet and along the flow path to cause sorption of the analyte by the sorbent material. Transferring the desorbed analyte into the chemical analyzer can include transferring different analytes desorbed from one or more sorbent material coatings on the heating element into the chemical analyzer. Transferring the desorbed analyte into the chemical analyzer can include actuating a flow control device between the desorption tube and the chemical analyzer.

In another aspect, a chemical analysis system features one or more of the pre-concentrators described above, and a chemical analyzer coupled to the pre-concentrator to receive analyte desorbed from the sorbent material. Optionally, the chemical analyzer can be a mass spectrometer. The heating element can define both a plurality of apertures through the heating element and a series of undulations spaced along the flow path, the plurality of apertures and the series of undulations forming a plurality of sorbent screens along the flow path and arranged such that flow along the flow path will be incident to the screens to enhance sorption of an analyte. Some systems may include a power source and the electrically conductive strip may include two electrodes coupled to the power source. Further, some systems may include control circuitry configured to evacuate the conduit to form a vacuum environment within the conduit. The control circuitry may be configured to conduct current through the heating element to desorb the analyte from the sorbent material after evacuating the conduit. In some cases, the control circuitry can be configured to conduct current through the heating element during a transfer of the analyte to the chemical analyzer to inhibit re-sorption of the analyte along the flow path.

Particular embodiments of the subject matter described in this specification can be implemented so as to realize one or more of the following advantages. The pre-concentrator may exhibit a substantially higher concentration gain thus enabling significantly improved sensitivity for a wide variety of chemical detection instrumentation. The improvement in thermal efficiency means that the overall response time of the pre-concentrator is substantially improved allowing deployments in scenarios where fast response is desirable (e.g., airport explosives screening). In addition to the security market, the pre-concentrator may also open new markets in healthcare and water analysis by providing a universal solution for both gas and liquid sampling. Improved desorption through quick and even heating with reduced power consumption may be accomplished by applying a sorbent coating directly on the heating element. In addition, the heating element design may provide an improved flow path and allow for multiple chemical species to be detected with single tube having multiple sorbent coatings. By directly coating a heater, the internal stresses caused by mismatches in thermal expansion may be minimized, thus improving the reliability of the device. By coating the heater directly, rather than relying upon multiple layers, the repeatability of the pre-concentrator can be improved.

The details of one or more embodiments of the subject matter described in this specification are set forth in the accompanying drawings and the description below. Other features, aspects, and advantages of the subject matter will become apparent from the description, the drawings, and the claims.

DESCRIPTION OF DRAWINGS

FIGS. 2A-2C are perspective views of an example mesh strip and tube.

FIG. 4 is a perspective view of an exemplary thermal desorption tube.

FIG. 5 is a flow diagram of a technique of operating a chemical analysis system.

FIG. 6 is a flow diagram illustrating the operation of a water sampling system.

Like reference symbols in the various drawings indicate like elements.

DETAILED DESCRIPTION

In the description below, for the purposes of explanation, specific examples related to introducing an analyte into a mass spectrometer for analysis have been set forth in order to provide a thorough understanding of the implementations of the subject matter described in this specification. It is appreciated that the implementations described herein can be utilized in other capacities as well and need not be limited to mass spectrometers. For example, implementations may be used to improve the operation of other chemical analyzers, including, for example, gas and liquid chromatographs, ion mobility spectrometers, surface acoustic wave sensors, electrochemical cells, and optical spectrometers (e.g., Raman, UV-VIS, NIR, and similar chemical detectors). Accordingly, other implementations are within the scope of the claims.

Figure 1:
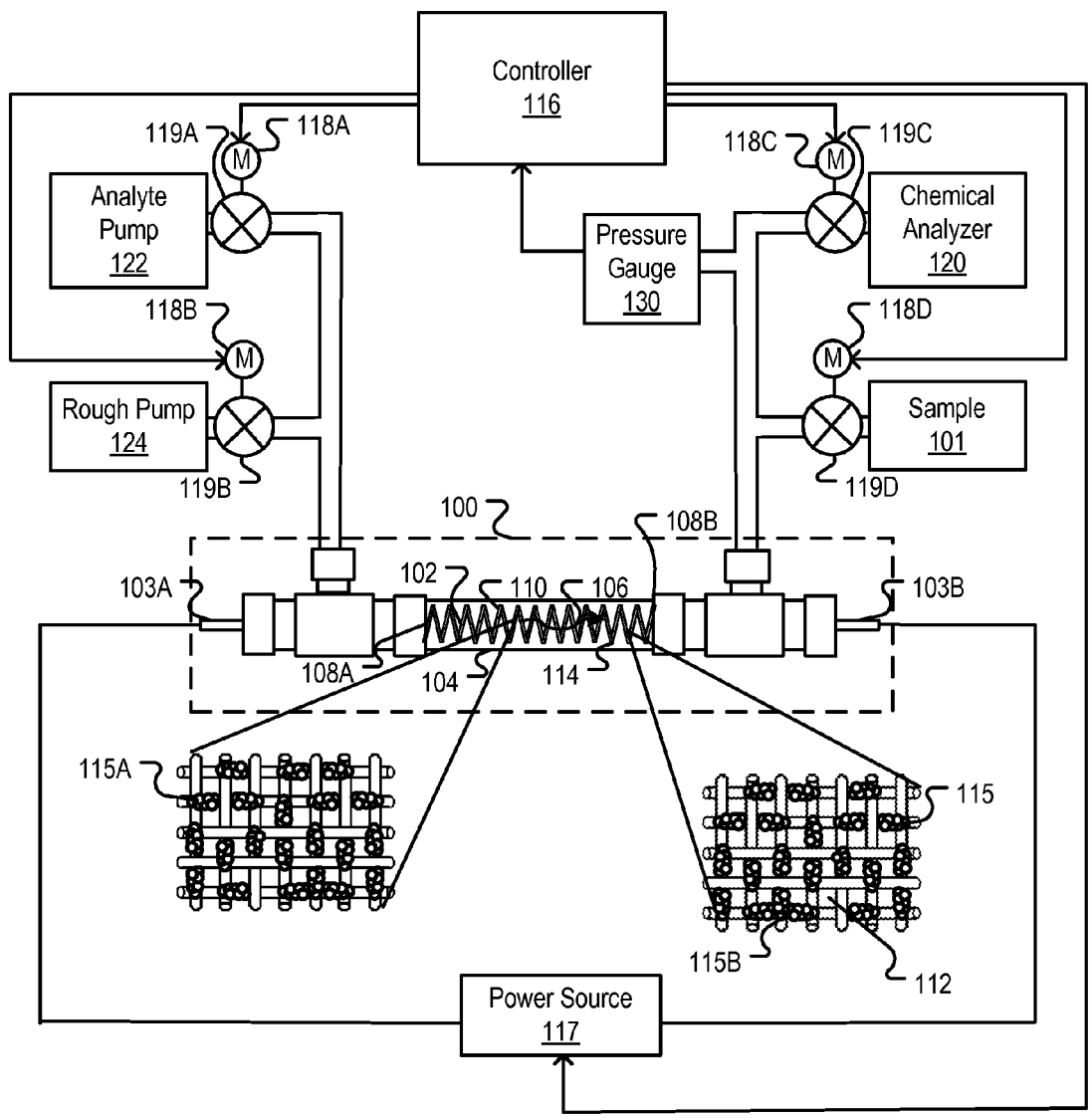
FIG. 1 is a system diagram of a chemical analysis system including a pre-concentrator inlet.

FIG. 1 illustrates a system diagram of an exemplary preconcentrator inlet 100 including a sorptive heating element (AHE) 102 disposed in a tube (e.g., stainless steel, quartz, or glass tube) forming a thermal desorption tube (TDT) 104. TDT 104 defines a flow path 106 between ends 108A and 108B. In some implementations, TDT 104 has a substantially rectangular internal cross-section transverse to the flow path. As described in more detail below, other implementations may include internal cross-sections having other shapes.

AHE 102 is formed from an electrically conductive strip 110 defining both a plurality of apertures 112 through the strip and a series of undulations 114 spaced along flow path 106. Strip 110 includes a coating 115 comprised of one or more sorbent materials for use in sorbing target chemicals for measurement and analysis. Strip 110 is coupled to a power source 117 via electrical leads/electrodes 103A, 103B. Power source 117 is coupled to a controller 116 and is configured to provide a variable voltage to AHE 102 to generate heat during sorption and/or desorption cycles in response to a control signal generated by controller 116. In this example, controller 116 includes an embedded microcontroller programmed to perform the sequence of operations described below. Alternative implementations include hardwired logic circuitry or analog circuitry, a computer, or a combination thereof. Controller 116 is also coupled to flow control device actuators, for example, valve actuators 118A-118D, and is configured to open and close flow control devices, such as, e.g., valves 119A-119D by transmitting an appropriate control signal to the corresponding valve actuator. In the implementation illustrated in FIG. 1, valves 119A-119D couple TDT 104 to a chemical analyzer 120 (e.g., a mass spectrometer), an analyte pump 122 for controlling the flow of analyte, and a rough pump 124 for evacuating TDT 104 prior to desorption to form a vacuum environment.

In some implementations, multiple thermal desorption tubes are coupled in parallel to provide redundancy or to increase the number of sorbents in flow path 106. Some examples include multiple thermal desorption tubes coupled in series to allow targeted collection, derivatization, etc. Further, in some examples, one or more thermal desorption tubes are coupled to multiple chemical analyzers 120 for redundant analysis, different analytical techniques, etc. Some configurations include a combination of these arrangements such that multiple thermal desorption tubes are coupled in a series-parallel arrangement to one or more chemical analyzers 120.

Referring again to FIG. 1, TDT 104 is connected directly to chemical analyzer 120 through valve 119C, however, some implementations may optionally include a flow control device, such as, for example, a flow restrictor, a pressure barrier, or a barrier membrane, between TDT 104 and chemical analyzer 120 to restrict the flow of analyte desorbed from sorbent material, and extracted from sample 101, into the chemical analyzer during desorption. In general, however, the flow control device can be omitted by utilizing the drag in high flow pumps coupled to chemical analyzer 120 (not shown) to introduce the analyte into the chemical analyzer and by reducing TDT 104 to the same pressure as the chemical analyzer chamber.

In most cases, the manufacture of strip 110 is determined so as to effect the largest surface area for a given planar area of material. In some examples, strip 110 is formed from a conductive wire mesh having a 30% open area and a wire diameter of 0.002 in. Alternative constructions of strip 110 include, for example, a woven wireframe, low density fibrous sheets (e.g. glass fiber sheets), graphite sheets (including graphene), and resistive sheets having chemically etched apertures. The strip material is selected such that its resistivity is sufficient to produce heat when current is passed through it. For example, in some implementations, a Nichrome wire is used.

Sorbent material is physically or chemically coated onto at least a portion of a sheet material used to form strip 110 using any suitable coating technique. For example, in some implementations, a sheet material is coated by passing the sheet through concentrated volumes of viscous liquid polymers under pressure and then heat curing at high temperature. Multiple passes may be implemented to achieve the desired coating thickness. Viscous liquid polymers can be provided in a solvent for coating. In other examples, a coating technique includes coating a commercial solid support such as, for example, Poropak P, Propak T, Tenax, and Carbosieve with a sorbent polymer. For example, a slurry can be formed that comprises Supelco® Carbosieve™ Mesh 80/100 or 177 to 149 μm, Polyethyleneimine (PEI), Polymethyl methacrylate (PMMA), or some other polymer, and a solvent. This slurry can then be coated on both sides of the sheet material.

In some implementations, portions of the sheet material are coated with different sorbents in a serial manner along the expected flow path and such that each strip 110 can sorb/desorb an increased number of chemicals in a single experiment without the need to change TDT 104 to collect different materials. For example, in FIG. 1, coating 115 includes a sorbent material 115A useful in sorbing hydrophobic materials (e.g., Carboxen 1016) and a sorbent material 115B useful in sorbing hydrophilic materials (e.g., Carbopak X). The use of additional sorbent coatings and alternative sorbent combinations and arrangements are also possible. For example, in some embodiments, one or more sorbents classified as weaker sorbents are arranged ahead of the stronger sorbent such that flow path 106 flows across the weaker sorbent first. In this way, a significant amount of easily attracted molecules are sorbed by the weaker sorbent prior to reaching the stronger sorbent so that the stronger sorbent can attract other molecules without first being saturated by the easily sorbed ones.

Once coated, the sheet material is cut or etched to form strips 110 and crimped to form undulations 114. In alternative implementations, the sheet material is sized to avoid the need to cut or etch the material to form strips 110. For example, in some instances, an electroformed mesh strip is coated and crimped to form strip 110. FIGS. 2A and 2B illustrate an example strip 110 coated with sorbent material 115A. In some examples, the coating thickness is between 3 μm and 20 μm. Other thicknesses are also possible.

In some implementations, the number of undulations 114 formed in strip 110 are determined to achieve a desired number of screens through which analyte molecules must pass along the flow path. The series of undulations form a plurality of sorbent surfaces (i.e., screens) along the flow path and are arranged such that flow along the flow path will be incident to the sorbent surfaces to enhance sorption of the analyte in sample 101. Further, in some implementations, the series of undulations are of a size, with respect to a cross-sectional area of the flow path, sufficient to increase local turbulence of an air flow along the flow path. By passing sample 101 through the orifices/apertures in multiple screens (e.g., 30+), the probability of an analyte molecule being sorbed by the pre-concentrator is increased substantially, thus improving the sensitivity and efficiency of system 100. In some examples, the probability of an analyte molecule being sorbed is increased by reducing the free space through which the sample can flow. For example, FIG. 2C illustrates an example tube 200 having inner cross-sectional dimensions approximately equal to the cross-sectional dimensions of crimped strip 110.

Figure 3A:
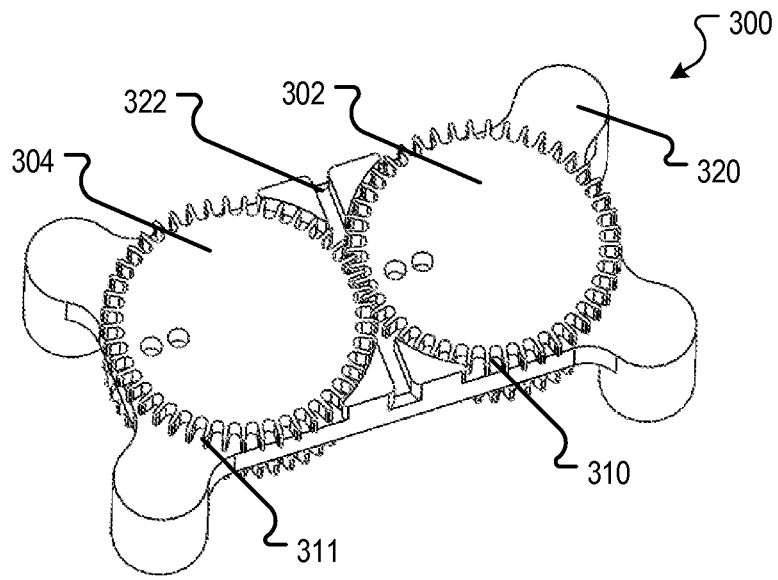
FIGS. 3A and 3B are perspective views of an exemplary crimping tool.
Figure 3B:
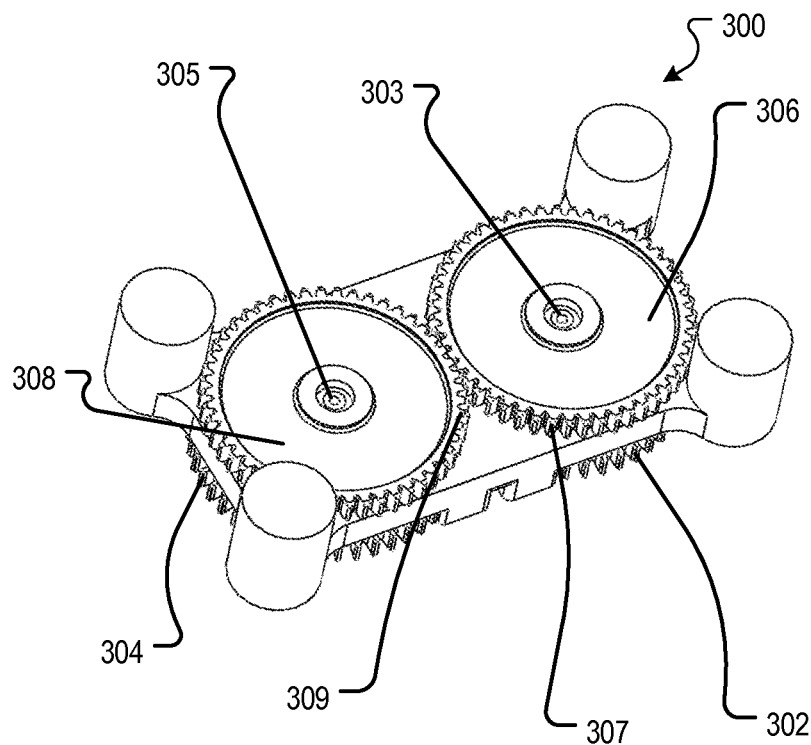

FIGS. 3A and 3B illustrate an exemplary crimping tool 300 for use in forming undulations 114. Crimping tool 300 includes crimping gears 302 and 304, each driven by a respective shaft 303, 305 coupled to drive gears 306, 308. The gear teeth of gears 302 and 304 are designed to be narrow enough so as to never contact each other, or contact the sorbent coating on more than one side at a time. In this way, the amount of sorbent coating removed during the crimping process is minimized. In some implementations, crimping gears 302, 304 are manufactured from a plastic material (e.g., nylon or polyacetal) to further minimize removal of the sorbent coating during the crimping process. Drive gear 306 includes a set of gear teeth 307 in meshing engagement with a corresponding set of gear teeth 309 on drive gear 308. Gear support 320 forms a channel 322 for guiding strip 110 into contact with the crimping gears. Undulations 114 are formed by feeding strip 110 into channel 322 while a drive gear actuator (not shown) rotates drive gears 306, 308, producing a corresponding rotation in crimping gears 302 and 304 causing them to grip strip 110 between an intermeshing set of teeth 310, 311 formed on the crimping gears. In alternative implementations, other techniques are used to form undulations 114 and/or to separate strip 110 from a base sheet material, including, for example, a rack and pinion assembly, or by using a stamping process.

Figure 7:
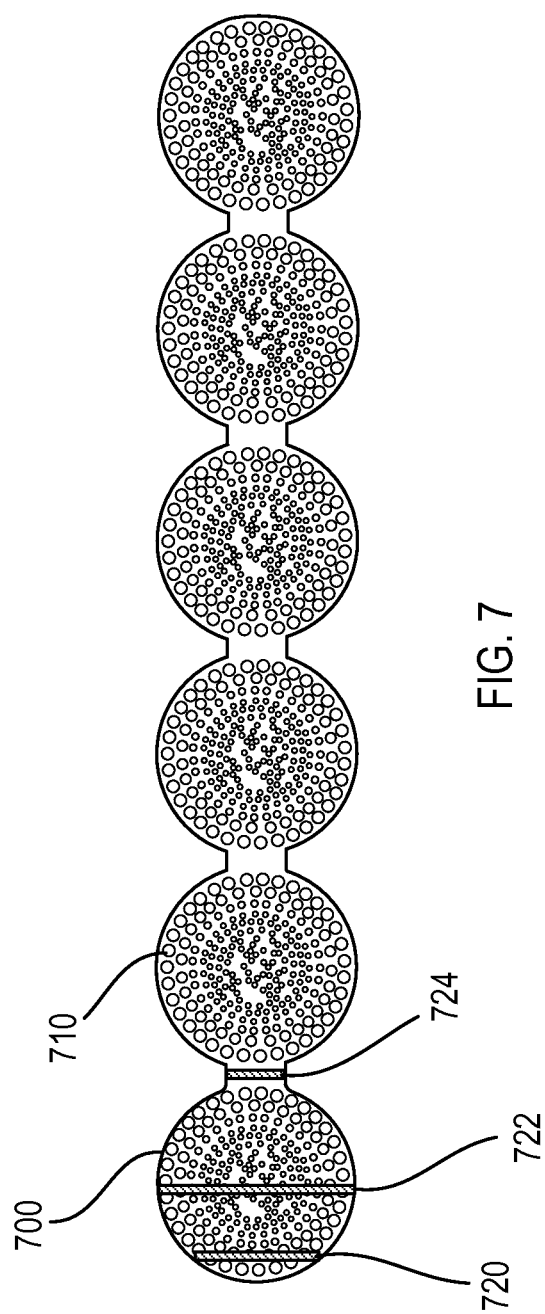
FIG. 7 is an exemplary strip having a varying shape along its length and a plurality of orifices of varying diameter.

In some implementations, strip 110 has a varying shape along its length and is configured to achieve constant heating, constant temperature, ease of manufacture, reduced flash and burring, or a combination of these and other phenomenon. For example, FIG. 7 illustrates a strip 700 having a varying shape along its length and a plurality of orifices 710 of varying diameter. To avoid hot spots, strip 700 maintains a uniform cross-sectional area along its length by varying the number and size of orifices and the cross-sectional width at each point along the strip. For example, cross-sections 720, 722, and 724 each have a cross-sectional resistance, R1, R2, R3, respectively, such that R1=R2=R3. Strip 700 and orifices 710 are chemically etched in a NiChrome sheet, thereby eliminating the need to cut the sheet material. Note, the size of the orifices in this illustration is exaggerated to illustrate the difference in sizes between orifices 710. In this way, strip 700 can be configured to fit in any shape tubing, including square, rectangular, circular, trapezoidal, triangular, etc. An additional benefit of etching strip 700 in this way includes the elimination of straggler filaments, created during the cutting of the sheet material, that catch when inserted into the tubing. Other benefits include minimal impact to the coating during forming, greater control of surface area and orifice sizes to yield, for example, 30%, 40%, 50% open area, better control of the flow path by controlling the size and placement of orifices 710. In addition, strip 700 can be manufactured to include an integrally formed terminal contact at each end facilitating better solder joints and/or mechanical connection alternatives to eliminate flux and solder outgassing.

Once formed and cut or etched to the desired length, strip 110 is soldered to electrical leads 103A, 103B and assembled into TDT 104. In some examples, the leads are mechanically coupled to strip 110, for example, by crimping, using connectors, or welding, thus avoiding the need for soldering. FIG. 4 illustrates a completed thermal desorption tube assembly 400 including a PTFE T-fitting 402, 404 at each end 108A, 108B of TDT 104. Other materials may also be used to form T-fittings 402, 404, including, for example, stainless steel, PEEK, PFA, FEP, PCTFE, Acetal, Nylon, and various other composite materials. The openings in fittings 402 and 404 can be sealed using a variety of means, including, without limitation, adhesives (e.g., Torr-Seal), pressure fit wires, and grommets.

FIG. 5 illustrates an example technique (500) for operating the system of FIG. 1 to introduce an analyte into the chemical analyzer. As illustrated, controller 116 introduces a sample by opening valves 119A and 119D and initiating a flow of analyte across and through AHE 102 (502). As the sample is drawn across the surface and through the apertures of AHE 102, one or more chemicals are sorbed by sorbent material coating 115. In some embodiments, a current is generated in AHE 102 by power source 117 during the sorption phase to generate heat in TDT 104 via Joule heating. In this way, a constant temperature is provided regardless of the environmental temperature, thus improving the operation of the pre-concentrator over a range of temperatures. Heating during the sorption phase may also be used to intentionally prevent or limit the sorption of some analytes. Further, the heat generated in TDT 104 effectively heats the portions of the system forming the analyte flow path.

After a sufficient amount of analyte has been sorbed by AHE 102, controller 116 closes valves 119A and 119D and opens valve 119B to begin evacuation (504). Rough pump 114 evacuates TDT 104 and reduces the pressure in TDT 104 to a desired level (506), thereby forming a vacuum environment.

The evacuation of substantially all of gas contained in TDT 104 prior to the desorption phase, effectively increases the concentration of chemicals introduced to chemical analyzer 120 over that of a chemical introduced from a non-evacuated housing. To further illustrate this concept, let the pre-concentrator gain due to sorption of analyte into the sorbent material and subsequent release into the 'dead volume', $G_{sorption}$, be defined by the inlet concentration and the resulting concentration of desorbed material:

$$G_{sorption} = C_{desorbed}/C_{inlet},$$

where $C_{inlet}$ is the inlet concentration and $C_{desorbed}$ is the resulting concentration of the desorbed material. $C_{inlet}$ is determined by the particular experiment and $C_{desorbed}$ is given by the amount of material collected, $m_{collected}$, over the volume into which it is desorbed, $V_{desorbed}$.

$$C_{desorbed} = m_{collected}/V_{desorbed}$$

The amount of material collected is dependent on the exposure time, the inlet stream at concentration $C_{inlet}$, and the flow rate, $Q_{sample}$, such that:

$$m_{collected} = \epsilon_{collection} \int C_{inlet} \times Q_{sample} dt,$$

where $\epsilon_{collection}$ is the collection efficiency of the coated mesh. Table 2 below illustrates a sample calculation of the gain due to sorption/desorption.

TABLE 2

| Sorbent Sorption | |
|---|---|
| Efficiency ($\epsilon_{collection}$) | 75% |
| Sorption Gain | |
| Inlet Concentration ($C_{inlet}$) | 40 pg/l |
| Inlet Flow rate ($Q_{sample}$) | 1.29 l/min |
| Sorption Time ($t_{sample}$) | 5.00 sec |
| Dead Volume ($V_{desorbed}$) | 1.00E−3 liters |
| Mass Sorbed ($m_{collected}$) | 3.225 pg |
| Desorb Concentration ($C_{desorbed}$) | 3225.00 pg/l |
| Sorbent Gain ($G_{sorption}$) | 80.6 |

For low partial pressures of analyte compared to partial pressures of background matrix, the gain due to the evacuation of the 'dead volume' to a reduced pressure is given by:

$$G_{evacuation} = P_{inlet}/P_{evacuated}$$

where $P_{inlet}$ is the pressure of the inlet stream and $P_{evacuated}$ is the reduced pressure in the dead volume after evacuation. This equation is only valid while $P_{evacuated}$ is greater than is or equal to the internal operating pressure of the detection instrument. For desorbed partial pressures substantially similar to the evacuated pressure, the gain is given by:

$$G_{evacuation} = P_{inlet}/(p_{evacuated} + p_{desorbed})$$

where $p_{evacuated}$ is the partial pressure of the background after evacuation and $p_{desorbed}$ is the partial pressure of the desorbed analyte. The net gain is given by: desorbed is $$G = G_{sorption} \times G_{evacuation}.$$

Table 3 below illustrates a sample calculation showing net gain that can be achieved both by sorption and evacuation of the dead volume.

TABLE 3

| Evacuation Gain | |
|---|---|
| Inlet Pressure ($P_{inlet}$) | 760 Torr |
| Evacuated Pressure ($P_{evacuated}$) | 3 Torr |
| Pressure Ratio | 253.33 |
| Evacuation Gain ($G_{evacuation}$) | 253.33 |
| Net Pre-concentrator Inlet Gain | |
| Sorption Gain ($G_{sorption}$) | 80.6 |
| Evacuation Gain (G) | 20418.67 |

Thus, a substantial pre-concentration gain can be achieved with the combination of highly sorbent materials and evacuation of dead volume in the pre-concentrator. Thus, with reference to the table above, an instrument with a lower detection limit of 1 ppm would be able to effectively alarm on chemicals at a concentration of 50 pptr, well below the threshold for common toxins.

Referring again to FIG. 5, once the evacuation is complete and the desired pressure level is reached, controller 116 closes valve 119B, opens valve 119C, and initiates the desorption cycle to introduce the analyte into chemical analyzer 120 (508). Power source 117 generates a current through AHE 102 to rapidly increase the temperature of the sorbent material coating 115 and to release the analyte into chemical analyzer 120 (510).

In some examples, the heating element is controlled such that the temperature imparted upon the collector, which may contain a plurality of analytes having different boiling points at the pressure present in TDT 104, allows one or more of the analytes to be released while retaining one or more analytes. In some implementations, the temperature of AHE 102 is adjusted in a pattern, and valve 119C is operated, such that analytes are released and introduced into chemical analyzer 120 at different times. In some examples, the pressure of TDT 104 is adjusted in a pattern, with either substantially constant temperature or a corresponding temperature profile, to allow selective release of analyte from TDT 104. The temperature of AHE 102 is controlled by adjusting the voltage and/or current applied to AHE 102.

In some implementations, the temperature of AHE 102 is measured directly, for example, by using a temperature sensor. However, in some instances, measuring the temperature of the sorbent may be difficult due to the low mass of the heater as compared to even the smallest temperature sensors (small thermocouples). In addition, attaching the temperature sensor and passing sensing leads through the tube may present additional difficulties and introduce system complexity. In some examples, the temperature is measured optically, thus avoiding the need to pass sensing leads through the tube.

In some examples, AHE 102 is used as a temperature sensor such that the element's temperature is sensed based on a known and predictable correlation between the resistance of the conductive material (e.g., NiChrome) and its temperature. Resistance can be measured by monitoring the voltage across and current through the heating element (i.e., R=V/I). This technique allows fast and dynamic temperature determination without the need to add an external temperature sensor (which can cause thermal lag, exhibit variation in measured vs. actual temperature due to poor contact, thermal mass of temperature sensor, etc.) or the complexities of adding a discrete thermal sensor within TDT 104 and the associated control circuitry.

After the desorption and introduction phase is complete (e.g., based on an elapsed period of time or a temperature threshold), controller 116 terminates the power being applied to AHE 102, closes valve 119C, and cools TDT 104 by opening valves 119A and 119D prior to reinitiating the sorption process. In some implementations, controller 116 maintains a current through AHE 102 until valve 119C is closed to inhibit re-sorption of the analyte along the flow path.

In some examples, pre-concentrator inlet system 100 is used to sample liquids. FIG. 6 is a flow chart describing the use of the pre-concentrator as a direct liquid sampler for liquid sampling. As described, a liquid sample is drawn into the pre-concentrator using a liquid sampling pump (610). The analyte is then sorbed from the liquid stream into the coated mesh (620). After a period of time has elapsed, a purge gas (e.g., nitrogen) is used to push the liquid out of the pre-concentrator (630). In some implementations, the pre-concentrator is then evacuated (640) as described above with respect to FIG. 4. The sorbent material is then heated by generating a current in the coated mesh (650) and introduced into the chemical analyzer (660).

In the examples described above, near real time analysis may be achieved by directly heating AHE 102 since the thermal mass of the heated portion of system 100 is significantly reduced when compared to an indirect heating method. Thus, the cycle time can also be reduced to less than 30 seconds. Further, by directly heating sorbent coating 115, the thermal efficiency is significantly increased. In addition, by evacuating TDT 104 to a reduced pressure, conductive and convective thermal losses are reduced. Therefore, in some implementations, pre-concentrator inlet system 100 is able to operate with less than 10 W of power (average)/30W of power (peak). Further, the evacuation of the TDT 104 increases the apparent gain, in some cases by approximately $10^2$-$10^3$, thereby increasing the overall gain of the pre-concentrator to approximately $10^3$-$10^5$.

Table 4 below provides measured pre-concentration gains for four sorbents resulting from techniques described herein. The gain for each sorbent was calculated by dividing the Total Ion Current (TIC) measured for the desorption cycle, $IC_{concentrator}$, by the TIC measured when the same analyte was inlet directly to the mass spectrometer, $IC_{direct}$, and is given by:

$$Gain = \frac{\int IC_{concentrator} dt}{\int IC_{direct} dt}$$

The ion current may be monitored for at least a candidate peak in the mass spectrum or for substantially the entire spectrum. As shown, gains for acetone ranged from 5567, for Carboxen 1016, to 59793, for Carobxen 1018. Gains for Ethyl Acetate ranged from 105630, for Carboxen 1016, to 377766, for Carboxen 1003.

TABLE 4

| Analyte | Direct | Carbopak X | Carboxen 1003 | Carboxen 1016 | Carboxen 1018 |
|---|---|---|---|---|---|
| Acetone | 1 | 22847 | 68524 | 5567 | 59793 |
| Ethyl Acetate | 1 | 243674 | 377766 | 105630 | 343388 |

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments, and it should be understood that the described components and systems can generally be integrated together in a single product or packaged into multiple products.

What is claimed is:

1. A chemical pre-concentrator for increasing the concentration of an analyte comprising:
    a conduit having an interior defining a flow path between a first end and a second end of the conduit;
    a heating element consisting of an electrical conductor with a sorbent material directly coated on at least a portion of a surface of the electrical conductor, wherein the heating element is disposed within the interior of the conduit;
    a first fitting component coupled to the first end of the conduit, the first fitting component having a first opening for the flow path into the conduit and having a first electrical lead extending through the first fitting component that is electrically connected to a first end of the heating element; and
    a second fitting component coupled to the second end of the conduit, the second fitting component having a second opening for the flow path into the conduit and having a second electrical lead extending through the second fitting component that is electrically connected to a second end of the heating element,
        wherein the flow path extends along a path through the first opening, through the conduit, and through the second opening, and
        wherein the first and second fitting components are configured to allow evacuation of the conduit, such that, during an evacuation, the flow path between the first and second ends of the conduit is evacuated.

2. The pre-concentrator of claim 1, wherein the coated heating element defines a series of undulations spaced along the flow path, such that at least a portion of the flow path will be incident to one or more undulations and to the sorbent material coated directly onto the undulating heating element.

3. The pre-concentrator of claim 2, wherein the heating element is a conductive strip having a substantially constant thickness, such that the undulations are present on both sides of the strip.

4. The pre-concentrator of claim 1, wherein the heating element is formed from a wire.

5. The pre-concentrator of claim 4, wherein the heating element is a wire mesh.

6. The pre-concentrator of claim 5, wherein the mesh is composed of nickel chromium (NiCr).

7. The pre-concentrator of claim 6, wherein the mesh is formed to have about 150 to about 300 lines per inch.

8. The pre-concentrator of claim 1, wherein the heating element is a metal strip having apertures through which at least a portion of the flow path may flow.

9. The pre-concentrator of claim 2, wherein the heating element is configured to define a plurality of apertures through the heating element, such that the apertures are configured to allow at least a portion of the flow path to flow through the apertures.

10. The pre-concentrator of claim 1, wherein the heating element is configured to define a plurality of apertures through the heating element, such that the apertures are configured to allow at least a portion of the flow path to flow through the apertures.

11. The pre-concentrator of claim 1, further including at least one valve configured to be used when evacuating the conduit, such that the evacuation forms an evacuated environment within the conduit.

12. The pre-concentrator of claim 11, further comprising control circuitry configured to control the at least one valve during the evacuation of the conduit.

13. The pre-concentrator of claim 12, wherein the control circuitry is configured to conduct current through the heating element to desorb at least one analyte from the at least one sorbent material after evacuating the conduit.

14. The pre-concentrator of claim 13, wherein the control circuitry communicates with at least one flow control device disposed within or coupled to the pre-concentrator.

15. The pre-concentrator of claim 1, wherein the heating element has a uniform cross-section and a substantially constant resistivity along a length of the heating element, and wherein the heating element is configured to provide a substantially constant temperature along the length of the heating element when heating.

16. A method of introducing an analyte into a chemical analyzer for analysis, the method comprising:
providing a flow path between a first end and a second end of a conduit and having a heating element disposed within the conduit, wherein the heating element consists of an electrical conductor with a sorbent material directly coated on at least a portion of a surface of the electrical conductor,
wherein a first fitting component is coupled to the first end of the conduit, the first fitting component having a first opening for the flow path into the conduit and having a first electrical lead extending through the first fitting component that is electrically connected to a first end of the heating element,
wherein a second fitting component is coupled to the second end of the conduit, the second fitting component having a second opening for the flow path into the conduit and having a second electrical lead extending through the second fitting component that is electrically connected to a second end of the heating element,
wherein the flow path extends along a path through the first opening, through the conduit, and through the second opening;
evacuating, through the first and second openings of the first and second fitting components, respectively, the conduit to form an evacuated environment within the conduit;
conducting current, via the first and second electrical leads, through the heating element in the vacuum environment in order to desorb the analyte from the sorbent material; and
introducing the desorbed analyte into the chemical analyzer.

17. The method of claim 16, wherein the heating element defines a series of undulations spaced along the flow path, and wherein the providing of the flow path further includes:
directing at least a portion of the flow path to be incident to one or more undulations and to the sorbent material directly deposited onto the undulating heating element.

18. The method of claim 17, wherein the heating element is configured to define a plurality of apertures through the heating element, such that the apertures are configured to allow at least a portion of the flow path to flow through the apertures.

19. The method of claim 16, wherein the heating element is configured to define a plurality of apertures through the heating element, such that the apertures are configured to allow at least a portion of the flow path to flow through the apertures.

20. The method of claim 16, wherein the current is conducted through the heating element to desorb at least one analyte from the at least one sorbent material after evacuating the conduit.

21. The method of claim 16, wherein the heating element has a uniform cross-section and a substantially constant resistivity along a current path of the heating element, and wherein the heating element is configured to provide a substantially constant temperature along the current path of the heating element when heating.

22. A chemical pre-concentrator for increasing a concentration of a sample, comprising:
a conduit having an interior defining a flow path that extends between a first end of the conduit and a second end of the conduit;
a heating element consisting of an electrical conductor disposed within the interior of the conduit at a location in the flow path between the first end of the conduit and the second end of the conduit; and
at least one sorbent material that is coated directly on the heating element, wherein the coated heating element is disposed in the interior of the conduit such that at least a portion of the flow path is incident upon the heating element;
a first fitting component coupled to the first end of the conduit, the first fitting component having a first opening for the flow path into the conduit and having a first electrical lead extending through the first fitting component that is electrically connected to a first end of the heating element; and
a second fitting component coupled to the second end of the conduit, the second fitting component having a second opening for the flow path into the conduit and having a second electrical lead extending through the second fitting component that is electrically connected to a second end of the heating element,
wherein at least the portion of the interior of the conduit containing the heating element has a cross-section, transverse to the direction of the flow path, that consists of the flow path, the thickness of the heating element, and the thickness of the sorbent material coated directly on the at least two opposing sides of the heating element,
wherein the flow path extends along a path through the first opening, through the conduit, and through the second opening, and
wherein the first and second fitting components are configured to allow evacuation of the conduit, such that, during an evacuation, the flow path between the first and second ends of the conduit is evacuated.

23. The pre-concentrator of claim 22, wherein the heating element has a substantially circular cross-section transverse to the direction of flow.

24. The pre-concentrator of claim 22, further including at least one valve configured to be used when evacuating the conduit, such that the evacuation forms an evacuated environment within the conduit.

25. The pre-concentrator of claim 24, further comprising control circuitry configured to control that at least one valve during an evacuation of the conduit.

26. The pre-concentrator of claim 25, wherein the control circuitry is configured to conduct current through the heating element to desorb at least one analyte from the at least one sorbent material after evacuating the conduit.

27. The pre-concentrator of claim 22, wherein the heating element is formed from a wire.

28. The pre-concentrator of claim 27, wherein the heating element is a wire mesh.

29. The pre-concentrator of claim 28, wherein the mesh is composed of nickel chromium (NiCr).

30. The pre-concentrator of claim 28, wherein the mesh is formed to have about 150 to about 300 lines per inch.

31. The pre-concentrator of claim 22, wherein the heating element is a metal strip having apertures through which at least a portion of the flow path may flow.

32. The pre-concentrator of claim 22, wherein the heating element is configured to define a plurality of apertures through the heating element, such that the apertures are configured to allow at least a portion of the flow path to flow through the apertures.

33. The pre-concentrator of claim 22, wherein a cross-section of the heating element has a size substantially equal to the cross-section of the interior of the conduit.

34. The pre-concentrator of claim 22, wherein a cross-section of the heating element has a shape corresponding to the cross-section of the interior of the conduit.

35. The pre-concentrator of claim 1, wherein the first fitting component is formed of a first t-fitting having the first opening and another opening for the first electrical lead and wherein the second fitting component is formed of a second t-fitting having the second opening and another opening for the second electrical lead.

36. The pre-concentrator of claim 16, wherein the first fitting component is formed of a first t-fitting having the first opening and another opening for the first electrical lead and wherein the second fitting component is formed of a second Witting having the second opening and another opening for the second electrical lead.

37. The pre-concentrator of claim 22, wherein the first fitting component is formed of a first t-fitting having the first opening and another opening for the first electrical lead and wherein the second fitting component is formed of a second t-fitting having the second opening and another opening for the second electrical lead.

* * * * *

UNITED STATES PATENT AND TRADEMARK OFFICE
CERTIFICATE OF CORRECTION

| | | |
|---|---|---|
| PATENT NO. | : 8,784,737 B2 | |
| APPLICATION NO. | : 13/367755 | |
| DATED | : July 22, 2014 | |
| INVENTOR(S) | : David Rafferty et al. | |

It is certified that error appears in the above-identified patent and that said Letters Patent is hereby corrected as shown below:

In the claims

Claim 36, column 15, line 17:

"Witting having the second opening and another opening for" should read --t-fitting having the second opening and another opening for--

Signed and Sealed this
Twenty-fourth Day of November, 2015

Michelle K. Lee
*Director of the United States Patent and Trademark Office*